United States Patent [19]

Fukaya et al.

[11] Patent Number: 4,613,614
[45] Date of Patent: Sep. 23, 1986

[54] PROSTAGLANDIN $I_2$ ESTER AND FAT EMULSION CONTAINING THE SAME

[75] Inventors: Chikara Fukaya, Osaka; Youichiro Naito, Yawata; Kazumasa Yokoyama, Toyonaka, all of Japan

[73] Assignee: The Green Cross Corporation, Osaka, Japan

[21] Appl. No.: 626,422

[22] Filed: Jun. 29, 1984

[30] Foreign Application Priority Data

Jul. 5, 1983 [JP] Japan ................. 58-122900

[51] Int. Cl.$^4$ ............... A61K 31/557; C07D 307/935; A61K 9/10
[52] U.S. Cl. .................... 514/469; 549/465; 424/78
[58] Field of Search .......... 549/465; 514/469

[56] References Cited

U.S. PATENT DOCUMENTS

| | | | |
|---|---|---|---|
| 4,207,332 | 6/1980 | Hayashi et al. | 549/465 |
| 4,303,671 | 12/1981 | Fitzpatrick | 514/469 |
| 4,430,340 | 2/1984 | Cho | 514/469 |
| 4,479,944 | 10/1984 | Hayashi et al. | 549/465 |

FOREIGN PATENT DOCUMENTS 55-85578  6/1980  Japan .
1229967  4/1971  United Kingdom ............. 514/938

OTHER PUBLICATIONS

Harrow et al., Textbook of Biochemistry 7th. Ed., W. B. Saunders, pp. 37 and 256–259 (1958).

Primary Examiner—Henry R. Jiles
Assistant Examiner—Bernard I. Dentz
Attorney, Agent, or Firm—Cushman, Darby & Cushman

[57] ABSTRACT

There is provided a new ester of prostaglandin of the formula

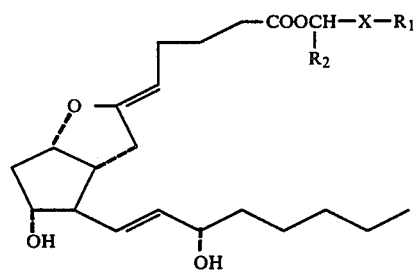

wherein $R_1$ denotes an alkyl group having 1 to 20 carbon atoms; $R_2$ denotes a hydrogen atom or a lower alkyl group having 1 to 4 carbon atoms; and X denotes a group represented by the formula

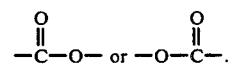

The new ester dissolves in oil easier than prostaglandin $I_2$ itself and can easily be emulsified in the form of particles of solution in a vegetable oil. The ester in the fat emulsion is more stable than prostaglandin $I_2$ and its physiological acts which are the same as prostaglandin $I_2$ are prolonged.

15 Claims, No Drawings

PROSTAGLANDIN I₂ ESTER AND FAT EMULSION CONTAINING THE SAME

This invention relates to a novel prostaglandin $I_2$ derivative.

Prostaglandin $I_2$ is known as a naturally occurring physiologically active substance. In chemical nomenclature, it is (5Z,13E)-(9α, 11α, 15S)-6,9-epoxy-11,15-dihydroxyprosta-5,13-dienoic acid of the formula

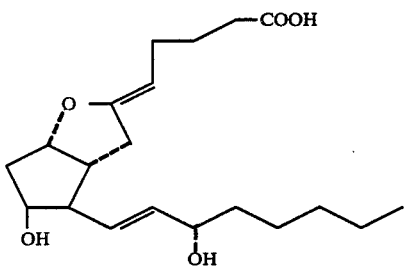

Some prostaglandin $I_2$ derivatives are known to be formed when prostaglandin $G_2$ (hereinafter referred to as $PGG_2$) or prostaglandin $H_2$ (hereinafter referred to as $PGH_2$) is incubated with microsomes of the equine arota, equine mesenteric artery, rabbit arota or rat fundus ventriculi. The prostaglandin $I_2$ derivative has a powerful artery-relaxative action. It acts specifically on the artery and does not relax other smooth muscles. Further, the prostaglandin $I_2$ derivative strongly suppresses the human platelet agglutination action induced by arachidonic acid. In view of the fact that thromboxan $A_2$ formed by similar incubation of $PGG_2$ or $PGH_2$ with platelet microsomes has an artery-contractive action and a platelet-agglutination action, the properties of prostaglandin $I_2$ mentioned above indicate that prostaglandin $I_2$ would play an important role in living bodies. Consequently, prostaglandin $I_2$ is believed to be effective for the treatment of arterial sclerosis, cardiac insufficiency, thrombosis and the like.

There are two problems to be met in developing prostaglandin $I_2$ preparations. In the first place, prostaglandin $I_2$ is chemically very unstable. When it is converted into its sodium salt or ester derivatives, the stability is improved to some extent but not so sufficiently. In the second place, prostaglandin $I_2$ has a half-life of its activity of only several minutes in physiological pH (pH 7.4), transforming itself into inactive 6-ketoprostaglandin $F_{1\alpha}$.

The reason for the instability of prostaglandin $I_2$ mentioned above is considered to be that, chemically, the vinyl ether structure having a double bond in $\Delta^5$-position is easily hydrated and, in living bodies, it is rapidly metabolized by the action of 15-position dehydrogenase.

The inventors have worked on developing a fat emulsion containing prostaglandin $I_2$ to overcome the two difficulties mentioned above. If prostaglandin $I_2$ could be formed into its fat emulsion, it would be expected that, since the prostaglandin $I_2$ would be protected by oil film, it would become less susceptible to such inactivation as hydration of the vinyl ether structure and oxisation by enzymes. Further, sustained release of prostaglandin $I_2$ can also be expected.

But actually prostaglandin $I_2$ is fairly water-soluble and is difficulty formed into fat emulsion. A fat emulsion can be formed more easily when the liposolubility of prostaglandin $I_2$ is increased by esterification thereof. But, since the esters have generally higher $ED_{50}$ values, they must be administered in larger amounts to develop the same degree of medicinal effect as that of prostaglandin $I_2$ itself.

Under these circumstances, the inventors, after extensive studies, have succeeded in creating a novel prostaglandin $I_2$ ester represented by the general formula (I)

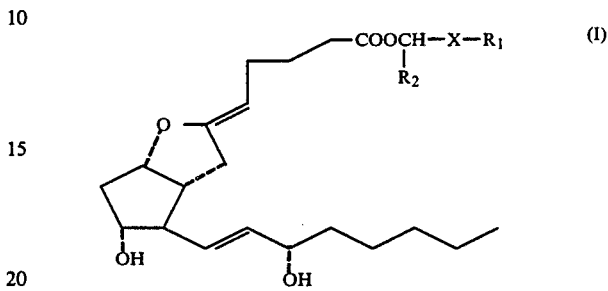

wherein $R_1$ denotes an alkyl group having 1 to 20 carbon atoms; $R_2$ denotes a hydrogen atom or a lower alkyl group having 1 to 4 carbon atoms; and X denotes a group represented by the formula

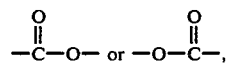

and also found that said ester can be made up very easily into a fat emulsion which renders prostaglandin $I_2$ structure stable and prolongs its effectivity with $ED_{50}$ value equivalent to or slightly more than prostaglandin $I_2$ itself.

Thus, this invention provides a prostaglandin $I_2$ ester represented by the general formula (I).

In the general formula (I), the alkyl group having 1 to 20 carbon atoms denoted by $R_1$ is of either branched or straight chain and includes, for example, methyl, ethyl, propyl, butyl, pentyl, hexyl, heptyl, octyl, nonyl, decyl, undecyl, dodecyl, tridecyl, tetradecyl, pentadecyl, heXadecyl, heptadecyl, octadecyl, nanodecyl, docosyl and the isomers thereof.

The lower alkyl group denoted by $R_2$ may be of either straight or branched chain and has preferably 1 to 4 carbon atoms. Examples of the lower alkyl group include methyl, ethyl, propyl, butyl and the isomers thereof.

The prostaglandin $I_2$ ester (I) according to this invention can be prepared, for example, by the following process.

That is, the process comprises reacting prostaglandin $I_2$ or its salt with an ester of the formula

wherein X, $R_1$ and $R_2$ are the same as defined above, and Xa is a halogen atom.

Since prostaglandin $I_2$ is very unstable, it is usual to employ its salt with an alkali metal, such as sodium, in this reaction.

In the general formula (II), examples of the halogen atom denoted by Xa include chlorine, bromine and iodine. Iodine is preferably used.

The reaction is carried out in the presence of a solvent and at a temperature of, usually, from 0° C. to room temperature. Examples of solvents which can be used include ethyl alcohol and tetrahydrofuran.

The reaction is preferably conducted in the presence of a phase transfer catalyst including, for examples, quaternary ammonium salts such as $(CH_3)_4NBr$, $(C_3H_7)_4NBr$ and $(C_4H_9)_4NHSO_4$. It is preferable then to conduct the reaction by using chlorinated alkanes such as methylene chloride and chloroform and under an anhydrous condition.

The prostaglandin $I_2$ ester of this invention can be easily isolated and purified by conventional methods including solution transfer, chromatography and recrystallization.

The prostaglandin $I_2$ ester (I) thus obtained is very soluble in oil and exerts artery-relaxative action and platelet-agglutination inhibitory action on mammals, and is of value as a drug for treating arterial sclerosis, cardiac insufficiency, thrombosis and the like. Although the prostaglandin $I_2$ ester (I) of this invention can be made up into preparations of optional dosage form by known methods, it can be easily and preferably formed into a fat emulsion preparation which renders the present ester less susceptible to inactivation.

The fat emulsion to which this invention relates can be prepared in a conventional manner. It is preferably emulsified by the aid of vegetable oils for dissolving the prostaglandin $I_2$ ester (I), such as soybean oil, cotton seed oil, sesame oil, safflower oil and corn oil.

Such emulsion preparation is exemplified by an emlulsion which comprises preferably 0.01 to 30% (w/v) of the prostaglandin $I_2$ ester (I), 5 to 50% (w/v), preferable 8 to 30% (w/v), of a vegetable oil, 1 to 50 parts, preferably 5 to 30 parts by weight of phospholipid based on 100 parts by weight of the vegetable oil, and the balance amount of water.

The symbol "% (w/v)" referred to in the specification and claims means the amount of a material by weight (gram) in 100 ml of the resulting emulsion.

The emulsion of this invention may contain further an amount of up to 0.3% (w/v) of a fatty acid having 6 to 22, preferably 12 to 20, carbon atoms or a physiologically acceptable salt thereof as an emulsifying adjuvant.

The emulsion preparation of this invention may contain a minor amount of stabilizer such as cholesterol and phosphatidic acid as well as a high molecular substance selected from albumin, dextran, vinyl polymer, nonionic surface active agent, gelatin and hydroxyethyl starch compounded therein.

It is also possible to add a conventional isotonifying agent such as glycerol and glucose for isotonification of the emulsion.

The fat emulsion of this invention is prepared, for example, by the following process.

Thus, predetermined amounts of prostaglandin $I_2$ ester (I), phospholipid, and, if necessary, the above-mentioned additives are mixed with a required amount of soybean oil, and the mixture is heated at 40° to 75° C. to form a solution. A required amount of water is added to the solution, and the mixture is emulsified at 20° to 80° by means of a conventional mixer (for example Homomixer) to give a crude emulsion. Stabilizers and isotonifying agents may be added at this stage.

The crude emulsion is then homogenized at 20° to 80° C. by using a homogenizer (for example, a pressure-jet type homogenizer such as Manton-Gaulin type homogenizer or an ultrasonic homogenizer) to obtain a homogenized, extremely fine fat emulsion containing the prastaglandin $I_2$ ester, which can be administered by intravenous injection. The emulsion has an average particle diameter of 1.0 μm or less and has an excellent stability against heat-sterilization and storage.

When a Manton-Gualin type homogenizer is used as the homogenizer, for example, the homogenization of crude emulsion is carried out, for example, passing the crude emulsion through the said homogenizer 0 to 2 times at the first-stage pressure of 100 to 150 kg/cm² and then 5 to 15 times under the second pressure of 400 to 700 kg/cm².

The prostaglandin $I_2$ ester (I) of this invention is administered, when used as medicine for treating human thrombosis in the form of fat emulsion, intravenously generally at a dose of 1 to 5 μg, preferably 3 to 6 μg, per one time for adults.

This invention is illustrated in more detail below with reference to Examples, but it is not limited thereto. The abbreviations IR and NMR used in Examples stand for infrared absorption spectroscopy and nuclear magnetic resonance spectroscopy, respectively.

EXAMPLE 1

Tetrabutylammonium hydrogen sulfate (10.2 mg, 0.03 mmol) was dissolved in 0.5 ml of water, and the solution was cooled with ice. Sodium salt (10.5 mg, 0.028 mmol) of prostaglandin $I_2$ was added to the cooled solution to dissolve completely. To the resulting solution, was added 1 ml of methylene chloride. After thorough shaking, the methylene chloride layer was collected by separation, and the aqueous layer was further mixed with 0.5 ml of methylene chloride to effect extraction. The extract was mixed with anhydrous sodium sulfate and dried thereover for 30 minutes. The drying agent was separated off from the mixture; the remaining liquid was then mixed with 12 mg of butyl iodoacetate and allowed to react at room temperature for 3 hours. After completion of the reaction, the reaction mixture was shaked well with 1 ml of water, the organic layer was then collected by separation and dried by adding anhydrous sodium sulfate thereto. After the drying agent had been filtered off, the solvent was evaporated off at room temperature by the use of a rotary evaporator to give a crude product. The product was purified by silica gel column chromatography using 2 g of silica gel to yield 8.3 mg (yield: 64%) of butoxycarbonylmethyl prostaglandin $I_2$ ester (compound 1) as a colorless oil. The eluant used in the chromatography was a hexane-ethyl acetate mixture (1:1) containing 1% triethylamine.

IR (liquid film method): 3400, 2950, 2850, 1755, 1730, 1450, 1240, 1180, 980 cm$^{-1}$.

NMR (CDCl$_3$ solution): 5.6 (2H, s), 5.1–5.5 (3H, m), 4.1 (2H, t), 0.9 (6H, m).

EXAMPLE 2

In the same procedures as in Example 1 but by using iodomethyl pivalate and other respective reactants in place of the butyl iodoacetate, the following compounds were obtained.

Pivaloyloxymethyl prostaglandin $I_2$ ester (compound 2)

Appearance: colorless oil; Yield: 58%.

IR (liquid film method): 3400, 2950, 2830, 1740, 1450, 1215, 1170, 960 cm$^{-1}$.

NMR (CDCl$_3$ solution): 5.7 (2H, s), 5.1–5.5 (3H, m), 1.1 (9H, s), 0.9 (3H, m).

Hexyloxycarbonylmethyl prostaglandin I$_2$ ester

Reactant: hexyl iodoacetate.
Appearance: colorless oil; Yield: 54%.
IR (liquid film method): 3400, 2950, 2830, 1750, 1725, 1450, 1235, 1175 cm$^{-1}$.
NMR (CDCl$_3$ solution): 5.6 (2H, s), 5.1–5.5 (3H, m), 4.1 (2H, t), 0.9 (6H, m).

Octyloxycarbonylmethyl prostaglandin I$_2$ ester

Reactant: Octyl iodoacetate.
Appearance: colorless oil; Yield: 49%.
IR (liquid film method): 3400, 2950, 2830, 1750, 1730, 1450, 1230, 1180 cm$^{-1}$.
NMR (CDCl$_3$ solution): 5.6 (2H, s), 5.1–5.5 (3H, m), 4.1 (2H, t), 0.9 (6H, m).

Cetyloxycarbonylmethyl prostaglandin I$_2$ ester

Reactant: cetyl iodoacetate.
Appearance: pale yellow oil; Yield: 38%.
IR (liquid film method): 3400, 2950, 2830, 1755, 1730, 1450, 1220, 1180, 955 cm$^{-1}$.
NMR (CDCl$_3$ solution): 5.6 (2H, s), 5.1–5.5 (3H, m), 4.1 (2H, t), 0.9 (6H, m).

Acetoxymethyl prostaglandin I$_2$ ester

Reactant: Iodomethyl acetate.
Appearance: colorless oil; Yield: 65%.
IR (liquid film method): 3400, 2950, 2830, 1745, 1450, 1250, 1170 cm$^{-1}$.
NMR (CDCl$_3$ solution): 5.7 (2H, s), 5.1–5.5 (3H, m), 2.1 (3H, s), 0.9 (3H, m).

Decanoyloxymethyl prostaglandin I$_2$ ester

Reactant: Iodomethyl decanoic acid ester.
Appearance: colorless wax; Yield: 45%.
IR (liquid film method): 3400, 2950, 2830, 1750, 1455, 1215, 1180 cm$^{-1}$.
NMR (CDCl$_3$ solution): 5.7 (2H, s), 5.1–5.5 (3H, m), 0.9 (6H, m).

1-Acetoxyethyl prostaglandin I$_2$ ester

Reagent: 1-Iodoethyl acetate.
Appearance: colorless oil; Yield: 58%.
IR (liquid film method): 3400, 2950, 2830, 1750, 1455, 1230, 1180, 940 cm$^{-1}$.
NMR (CDCl$_3$ solution): 6.1 (1H, q), 5.1–5.5 (3H, m), 2.1 (3H, s), 1.1 (3H, d), 0.9 (3H, m).

1-Hexanoyloxyethyl prostaglandin I$_2$ ester (compound 3)

Reagent: 1-Iodoethyl hexanoic acid ester.
Appearance: colorless oil; Yield: 51%.
IR (liquid film method): 3400, 2950, 2830 1740, 1455, 1230, 1175, 960 cm$^{-1}$.
NMR (CDCl$_3$ solution): 6.1 (1H, q), 5.1–5.5 (3H, m), 1.1 (3H, d), 0.9 (6H, m).

1-Decanoyloxyethyl prostaglandin I$_2$ ester

Reagent: 1-Iodoethyl decanoic acid ester.
Appearance: pale yellow oil; Yield: 43%.
IR (liquid film method): 3400, 2950, 2830, 1750, 1450, 1225, 1175, 960 cm$^{-1}$.
NMR (CDCl$_3$ solution): 6.1 (1H, q), 5.1–5.5 (3H, m), 1.1 (3H, d), 0.9 (6H, m).

EXAMPLE 3

Into 100.0 g of purified soybean oil, were added 24.0 g of purified egg-yolk phospholipid, 10 mg of pivaloyloxymethyl prostaglandin I$_2$ ester, 0.5 g of phosphatidic acid and sodium oleate, and the resulting mixture was heated at 40° to 75° C. to form a solution. To the solution, was added 1000 ml of distilled water, and the mixture was passed through a Manton-Gaulin type homogenizer 10 times under a first-stage pressure of 100 Kg/cm$^2$ and a total pressure of 450 Kg/cm$^2$ to form an emulsion. The emulsion was then mixed with 5.0 g of glycerol, mixed further with 400 ml of distilled water for injection at 20° to 40° C., and formed into a coarse emulsion by using a Homomixer. The coarse emulsion was again passed through a Manton-Gaulin type homogenizer 10 times under a first-stage pressure of 120 Kg/cm$^2$ and a total pressure of 500 Kg/cm$^2$ to form an emulsion. Thus, there was obtained a homogeneous and very finely dispersed fat emulsion containing the prostaglandin I$_2$ derivative mentioned above. The emulsion, 0.2 to 0.4$\mu$ in average diameter of dispersed droplets, contained none of the droplets of 1$\mu$ or above in size.

EXPERIMENTAL EXAMPLE 1

Wistar-strain male rats weighing 150 to 200 g were used in the experiment.

Blood samples were collected from the heart of the animal without anasthesia by the use of a syringe, in which 3.3% sodium citrate solution had been placed beforehand, in such a way that the volume ratio of the sodium citrate solution to the collected blood was 1:9. The collected blood was then quickly centrifuged at 170 G at room temperature to obtain plasma rich in platelet (hereinafter referred to as PRP).

Then, the compounds 1, 2 and 3 as well as sodium salt of prostaglandin I$_2$ were respectively dissolved in ethanol to a concentration of 1 mg/ml in terms of prostaglandin I$_2$, and thereafter diluted with physiological saline to form solutions of various concentrations.

The platelet-agglutination inhibition test was carried out in the following manner.

The above-mentioned PRP (500 $\mu$l) and the above solution 50 $\mu$l) containing the drug tested were incubated at 37° C. for one minute in an aggregometer cuvette; then 1 mM adenosine phosphate solution (50 $\mu$l) was added to the mixture to obtain an agglutination curve on the instrument and determine the maximum agglutination rate. A mixture of 500 $\mu$l of PRP, 50 $\mu$l of physiological saline and 50 $\mu$l of 1 mM adenosine phosphate solution was used as the control to obtain similarly an agglutination curve.

The concentration (ED$_{50}$) in terms of prostaglandin I$_2$ of each of the drugs to be tested, at which the solution containing the drug reduces the percentage of the maximum agglutination rate by 50% relative to that of the control taken as 100, was calculated.

The results are shown in Table 1.

Separately, by using fat emulsions prepared as in Example 3 and extending the incubation time to 5, 20 and 60 minutes, the changes in agglutination-inhibition rate were observed. Each fat emulsion was prepared to contain 1 mg in terms of prostaglandin I$_2$ of a test compound. It was incubated with PRP for a predetermined time; the platelets were then washed; and the content of c-AMP in the platelets was determined, thus to evaluate indirectly the inhibitory action on platelet agglutination. A physiological saline solution of sodium salt of prostaglandin $I_2$ was used as the control.

The results obtained are shown in Table 2.

These results reveal that the prostaglandin $I_2$ derivative (I) of this invention has an effect equivalent to that of prostaglandin $I_2$, can be made up into a fat emulsion and can thus release the medicinal effect sustainedly.

TABLE 1

| Compound | Ed$_{50}$ (μg/ml) |
|---|---|
| Compound 1 | 4.6 |
| Compound 2 | 0.5 |
| Compound 3 | 0.7 |
| Sodium salt of prostaglandin $I_2$ | 0.4 |

TABLE 2

| Compound in fat emulsion | Incubation time (minute) | | | |
|---|---|---|---|---|
| | 1 | 5 | 20 | 60 |
| Compound 1 | 13% | 11% | 7% | 3% |
| Compound 2 | 93% | 78% | 51% | 27% |
| Compound 3 | 78% | 71% | 65% | 48% |
| Sodium salt of prosataglandin $I_2$ (aq. solution) | 100% | 17% | 0% | 0% |

What is claimed is:

1. A prostaglandin $I_2$ ester represented by the formula

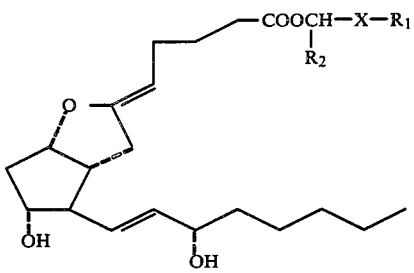

wherein $R_1$ denotes an alkyl group having 1 to 20 carbon atoms; $R_2$ denotes a hydrogen atom or a lower alkyl group having 1 to 4 carbon atoms; and X denotes a group represented by the formula

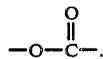

2. The prostaglandin $I_2$ ester of claim 1, which is pivaloyloxymethyl prostaglandin $I_2$ ester.

3. The prostaglandin $I_2$ ester of claim 1, which is acetoxymethyl prostaglandin $I_2$ ester.

4. The prostaglandin $I_2$ ester of claim 1, which is decanoyloxymethyl prostaglandin $I_2$ ester.

5. The prostaglandin $I_2$ ester of claim 1, which is 1-acetoxyethyl prostaglandin $I_2$ ester.

6. The prostaglandin $I_2$ ester of claim 1, which is hexanoyloxyethyl prostaglandin $I_2$ ester.

7. The prostaglandin $I_2$ ester of claim 1, which is decanoyloxyethyl prostaglandin $I_2$ ester.

8. A pharmaceutical fat emulsion comprising a physiologically acceptable emulsifier, water and particles of a vegetable oil containing an effective amount of at least one ester of prostaglandin $I_2$ of the formula

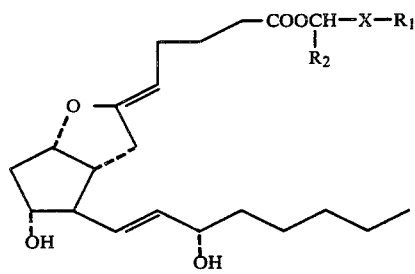

where $R_1$ denotes an alkyl group having 1 to 20 carbon atoms; $R_2$ denotes a hydrogen atom or a lower alkyl group having 1 to 4 carbon atoms; and X denotes a group represented by the formula

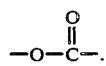

9. A pharmaceutical emulsion of claim 8 wherein the physiologically acceptable emulsifier is a phospholipid.

10. A pharmaceutical emulsion of claim 8 wherein the vegetable oil is soybean oil.

11. A pharmaceutical emulsion of claim 8 wherein an effective amount as an emulsifying adjuvant of a fatty acid having 6 to 22 carbon atoms or a physiologically acceptable salt thereof is further contained.

12. A pharmaceutical emulsion of claim 8 wherein a stabilizing amount of a chlolesterol, phosphatidic acid or mixture thereof is further contained as a stabilizer.

13. A pharmaceutical emulsion of claim 8 wherein a stabilizing amount of an albumin, a dextran, a vinylpolymer, nonionic surface active agent, gelatin or a hydroxyethyl starch is further contained.

14. A pharmaceutical emulsion of claim 8 wherein an isotonifying amount of glycerol and/or glucose is further contained.

15. A pharmaceutical emulsion of claim 8, comprising 5 to 50% (w/v) of a vegetable oil in which 0.01 to 30% (w/v) based on the emulsion of the ester of prostaglandin $I_2$ is dissolved, 1 to 50 parts by weight based on 100 parts by weight of the vegetable oil, a phospholipid, and the balance water.

* * * * *